(12) United States Patent
Lane et al.

(10) Patent No.: US 11,915,826 B2
(45) Date of Patent: Feb. 27, 2024

(54) DIGITAL IMAGE SCREENING AND/OR DIAGNOSIS USING ARTIFICIAL INTELLIGENCE

(71) Applicant: Welch Allyn, Inc., Skaneateles Falls, NY (US)

(72) Inventors: John A. Lane, Weedsport, NY (US); Chris R. Roberts, Skaneateles, NY (US); Thomas A. Gurgol, Skaneateles, NY (US); WonKyung McSweeney, Syracuse, NY (US)

(73) Assignee: Welch Allyn, Inc., Skaneateles Falls, NY (US)

(*) Notice: Subject to any disclaimer, the term of this patent is extended or adjusted under 35 U.S.C. 154(b) by 297 days.

(21) Appl. No.: 15/929,978

(22) Filed: Jun. 1, 2020

(65) Prior Publication Data

US 2020/0388383 A1 Dec. 10, 2020

Related U.S. Application Data

(60) Provisional application No. 62/858,579, filed on Jun. 7, 2019.

(51) Int. Cl.
*G16H 50/20* (2018.01)
*A61B 3/00* (2006.01)
(Continued)

(52) U.S. Cl.
CPC .......... *G16H 50/20* (2018.01); *A61B 3/0025* (2013.01); *A61B 3/12* (2013.01); *G16H 30/20* (2018.01); *G16H 80/00* (2018.01)

(58) Field of Classification Search
CPC ........ G16H 50/20; G16H 30/20; G16H 80/00; G16H 30/40; G16H 50/30; A61B 3/0025;
(Continued)

(56) References Cited

U.S. PATENT DOCUMENTS 6,277,067 B1* 8/2001 Blair .................... A61B 1/0004
600/167
2002/0052551 A1* 5/2002 Sinclair .................. G16H 40/67
128/920

(Continued)

FOREIGN PATENT DOCUMENTS

WO 2018/094381 A1 5/2018
WO 2018/201633 A1 11/2018
(Continued)

OTHER PUBLICATIONS

U.S. Appl. No. 62/706,324, filed Aug. 10, 2020, entitled "Eye Imaging Devices".
(Continued)

*Primary Examiner* — Siamak Harandi
(74) *Attorney, Agent, or Firm* — Merchant & Gould P.C.

(57) ABSTRACT

An example device is configured to capture an image of a patient. The devices includes a camera configured to capture the image of the patient. The device further: captures contextual data associated with the image; allows a caregiver to select the image to be stored; forwards the image and the contextual data to a remote server for processing using artificial intelligence; and receives a proposed diagnosis from the remote server based upon the image and the contextual data.

11 Claims, 5 Drawing Sheets

(51) Int. Cl.
*A61B 3/12* (2006.01)
*G16H 30/20* (2018.01)
*G16H 80/00* (2018.01)

(58) Field of Classification Search
CPC ......... A61B 3/12; G06T 7/0012; G06F 16/55; G06F 16/583
See application file for complete search history.

(56) References Cited

U.S. PATENT DOCUMENTS

| | | | | |
|---|---|---|---|---|
| 2005/0049497 | A1* | 3/2005 | Krishnan | G16H 50/20 600/437 |
| 2007/0021677 | A1* | 1/2007 | Markel | A61B 5/0006 600/509 |
| 2007/0239491 | A1* | 10/2007 | Rao | H04L 12/4633 705/3 |
| 2008/0312959 | A1* | 12/2008 | Rose | G16H 10/60 705/2 |
| 2009/0216556 | A1* | 8/2009 | Martin | G16H 40/63 705/3 |
| 2012/0016691 | A1* | 1/2012 | Sievenpiper | G16H 40/20 705/2 |
| 2012/0163775 | A1* | 6/2012 | Banerjee | H04N 9/8042 386/E5.028 |
| 2016/0331342 | A1* | 11/2016 | Garcia | A61B 6/4494 |
| 2017/0119241 | A1* | 5/2017 | Farchione | A61B 3/12 |
| 2018/0214087 | A1 | 8/2018 | Balaji et al. | |
| 2018/0315193 | A1 | 11/2018 | Paschalakis et al. | |
| 2019/0110753 | A1 | 4/2019 | Zhang et al. | |
| 2019/0221313 | A1 | 7/2019 | Rim et al. | |
| 2020/0160521 | A1* | 5/2020 | Wang | G06V 40/197 |
| 2020/0196861 | A1 | 6/2020 | Hart et al. | |
| 2020/0202529 | A1 | 6/2020 | Hart et al. | |
| 2021/0315541 | A1* | 10/2021 | Poland | A61B 8/56 |

FOREIGN PATENT DOCUMENTS

| | | |
|---|---|---|
| WO | 2019/039912 A1 | 2/2019 |
| WO | 2019/087209 A1 | 5/2019 |

OTHER PUBLICATIONS

Extended European Search Report for Application No. 20178267.9 dated Nov. 12, 2020 (8 pages).

* cited by examiner

DIGITAL IMAGE SCREENING AND/OR DIAGNOSIS USING ARTIFICIAL INTELLIGENCE

INTRODUCTION

Many diseases can be diagnosed and treated by studying images taken of the patient. For example, diabetic retinopathy can be diagnosed by studying an image of the retina. Such images can be captured and reviewed manually by a caregiver. However, manual review is a labor-intensive process and subject to error.

SUMMARY

In one aspect, an example device is configured to capture an image of a patient. The devices includes a camera configured to capture the image of the patient. The device further: captures contextual data associated with the image; allows a caregiver to select the image to be stored; forwards the image and the contextual data to a remote server for processing using artificial intelligence; and receives a proposed diagnosis from the remote server based upon the image and the contextual data.

DESCRIPTION OF THE FIGURES

The following drawing figures, which form a part of this application, are illustrative of described technology and are not meant to limit the scope of the disclosure in any manner.

DETAILED DESCRIPTION

Figure 1:
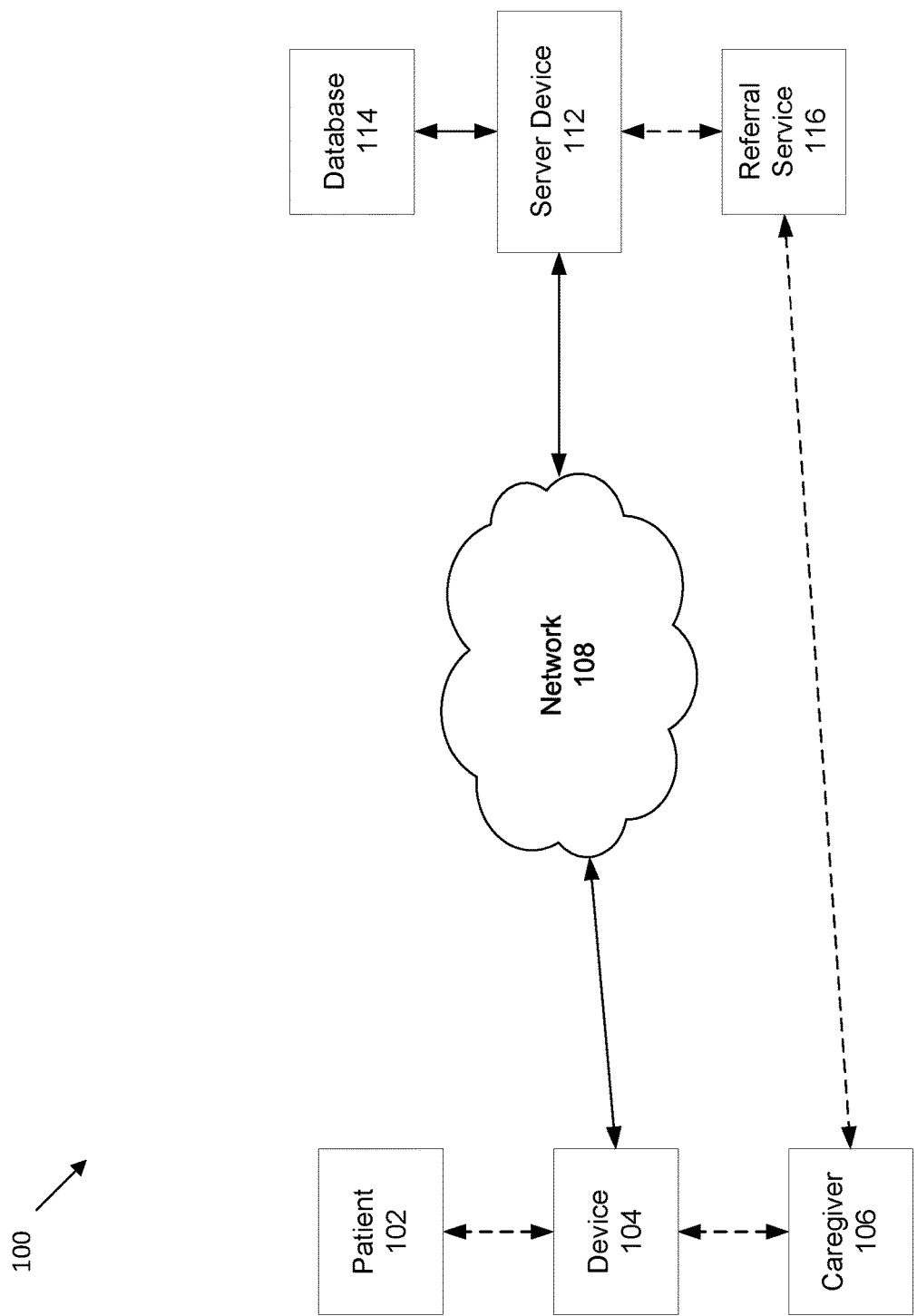
FIG. 1 shows an example system for capturing images of a patient.

FIG. 1 is a schematic block diagram illustrating an example system 100 for capturing images of a patient for screening and/or diagnosis of the patient. In the example described herein, the system is a fundus imaging system. However, in other embodiments, the system can be used to: capture images of the skin to look for carcinoma; capture images of the tympanic membrane to look for otitis media; and/or capture images of the eyes to look for cataracts.

The example system 100 includes a patient 102, an imaging device 104, and a server device 112 connected to the imaging device 104 through a network 108.

The imaging device 104 functions as an ophthalmoscope to create a set of digital images of the fundus of the eye of the patient 102. As used herein, "fundus" refers to the eye fundus and includes the retina, optic nerve, macula, vitreous, and/or choroid and posterior pole.

As noted, other types of medical devices can be used that include built-in illumination, optics, and image capture. Such devices include: an otoscope that is configured to capture images of the tympanic membrane; a dermatoscope that is configured to capture images of the skin; or a colposcope that is configured to capture images of the vagina.

In this example, one or more images of the eye are desired. For instance, the patient 102 is can be screened for an eye disease, such as diabetic retinopathy. The imaging device 104 can also be used to provide images of the eye for other purposes, such as to diagnose or monitor the progression of a disease such as diabetic retinopathy.

The imaging device 104 includes a handheld housing that supports the components of the imaging device 104. The housing supports one or two apertures for imaging one or two eyes at a time. In embodiments, the housing supports positional guides for the patient 102, such as an optional adjustable chin rest. The positional guide or guides help a caregiver 106 to align the patient's eye or eyes with the one or two apertures. In embodiments, the housing supports means for raising and lowering the one or more apertures to align them with the patient's eye or eyes. Once the patient's eyes are aligned, the caregiver 106 then initiates the image captures by the imaging device 104.

Images can be captured in still form or in video form. In video form, a motion video of a certain duration can be captured and/or a live video stream can be captured and provided, for example, to a remote device such as the server device 112.

The example imaging device 104 is connected to the server device 112 through the network 108. The network 108 may include any type of wireless network, a wired network, or any communication network known in the art. For example, wireless connections can include cellular network connections and connections made using protocols such as 802.11a, b, and/or g. In other examples, a wireless connection can be accomplished directly between the imaging device 104 and an external display using one or more wired or wireless protocols, such as Bluetooth, Wi-Fi Direct, radio-frequency identification (RFID), or ZigBee. Other configurations are possible.

The server device 112 receives data from the imaging device 104. Such data can include images captured of the patient 102, such as one or more fundus images. The data can also include contextual information associated with the images and/or patient 102. The server device 112 can include artificial intelligence, such as machine learning and/or neural network, that allows the server device 112 to analyze the data from the imaging device 104 and provide feedback to the patient 102, as described further below.

For example, the server device 112 can be implemented as one or more computing devices in the cloud that are networked to provide processing power. The server device 112 can be connected to a database 114 to access data from a large number of patients. This data can be analyzed using artificial intelligence to provide a meaningful analysis of the images and contextual data from the patient 102. The server device 112 can, in turn, provide suggested diagnoses diagnosis or probability of disease states and/or supporting logic to a caregiver 106 based upon that analysis.

In some examples, the server device 112 can be configured to communicate with a referral service 116. Upon an initial suggested diagnosis by the server device 112, the server device 112 can communicate the image, any contextual data associated therewith, and the preliminary diagnosis to the referral service 116. The referral service 116 can include, for example, specialists in the particular area of medicine. For example, a specialist at the referral service 112 can review the images, the contextual data associated therewith, and the preliminary diagnosis, and either confirm or modify the diagnosis. The diagnosis from the referral service 116 can be communicated back to the caregiver 106.

The system 100 can be used to assist the caregiver 106 in screening for, monitoring, or diagnosing various eye diseases, such as hypertension, diabetic retinopathy, glaucoma and papilledema.

Figure 2:
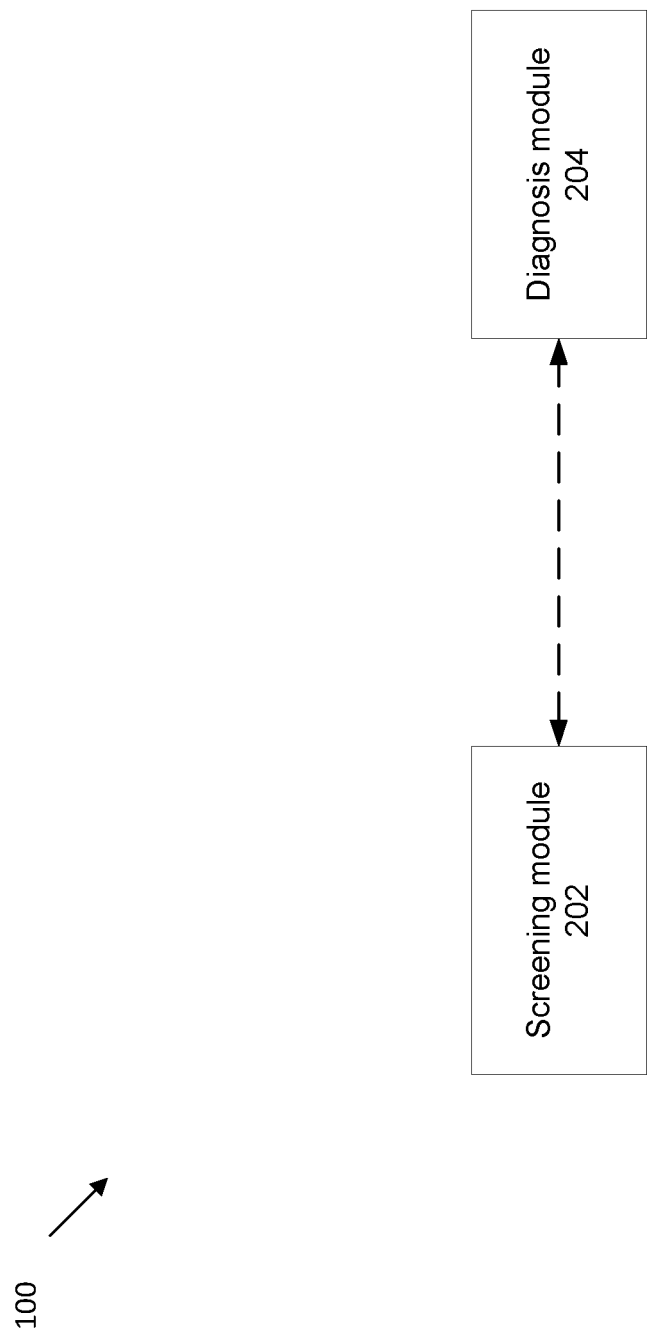
FIG. 2 shows example logical components of the system of FIG. 1.

For example, referring to FIG. 2, the system 100 is shown in schematic form. In this example, the system 100 includes two logical modules, a screening module 202, and a diagnosis module 204.

The screening module 202 assists the caregiver 106 in capturing data from the patient to screen the patient for various disease states. For example, as provided herein, the screening module 202 can assist the caregiver in capturing one or more images of the fundus of the eyes of the patient 102 using the imaging device 104. The screening module 202 can further assist the caregiver in capturing contextual information associated with the patient 102 that will be helpful in later diagnosis of the patient 102.

In the example shown, the screen module 202 is implemented in logic stored on the imaging device 104. In this manner, the imaging device 104 assists the caregiver in capturing images and contextual information to screen the patient 102. See FIG. 3 for additional information.

The diagnosis module 204 assists the caregiver 106 in diagnosis of the patient 102 with one or more disease states. The diagnosis module 204 analyzes the images and contextual data captured by the caregiver using the imaging device 104. This analysis, in turn, allows the system 100 to provide a suggested diagnosis to the caregiver.

In the example shown, diagnosis module 204 is implemented in logic stored on the server device 112. In this manner, the server device 112 assists the caregiver 106 in diagnosing any disease states of the patient 102. See FIG. 4 for additional information.

More specifically, in the example provided, the caregiver 106 interacts with the diagnosis module 204 directly, where the trained model for providing the diagnosis resides. The diagnosis module 204 interacts with the screening module 202 to provide either the diagnosis or request for new images (based on the accuracy score mentioned later.) All or subset of images captured are sent to the database to be used for later model training.

The server device 112 is where the continuous (or batch) training of the model occurs. When the model updates are available, the updates are pushed out to the diagnosis module 204 (regularly or triggered by certain condition).

Figure 3:
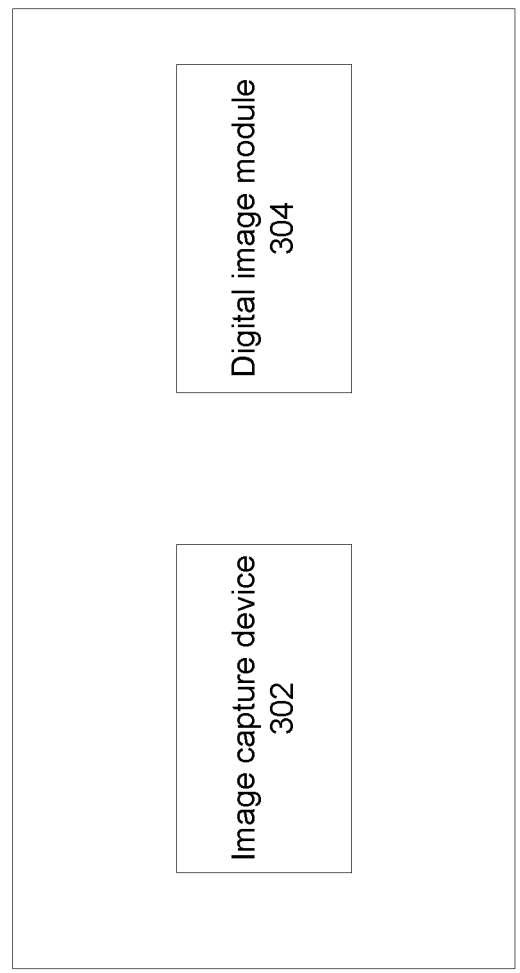
FIG. 3 shows example logical components of an imaging device of the system of FIG. 1.

Referring now to FIG. 3, additional details of the imaging device 104 are shown. In this example, the imaging device 104 includes an image capture device 302 and a digital image module 304.

The image capture device 302 includes one or more cameras used to capture an image of the patient 102, such as the fundus. Additional details of such a camera and its function are provided in U.S. patent application Ser. No. 16/229,939 filed on Dec. 21, 2018, the entirety of which is hereby incorporated by reference.

The digital image module 304 assists the caregiver 106 in capturing the necessary images using the image capture device 302. In this example, the digital image module 304 provides a workflow that assists the caregiver in capturing the digital images, as well as additional contextual data associated with the patient 102.

In some examples, the digital image module 304 is incorporated logically as part of the device 104 that captures the images of the patient 102. In another example, the digital image module 304 is incorporated in a standalone device that interfaces with the device 104 to assist in the capture of the images. In a specifically example, the digital image module 304 can be incorporated as an application running on a mobile device such as a smartphone or tablet computer. Other configurations are possible.

As part of the workflow for capturing the images, the digital image module 304 can assist the caregiver 106 in capturing and selecting images of the desired quality for diagnosis. For example, the digital image module 304 can help the caregiver to capture images of the proper lighting and quality. Further, the digital image module 304 can help the caregiver select certain images for storage and forwarding to the server device 112 and/or a medical records device like an EMR.

In another example, the digital image module 304 can require the caregiver 106 to input or otherwise obtain (e.g., through a feed from the EMR) contextual data associated with the patient and/or the capture of the images. This contextual data can include bibliographic information associated with the patient 102, such as age, gender, weight, height, etc. The contextual data could also include such information as previous health, patient diagnoses, drug regimes, and/or health history.

The contextual data can be notes captured by the caregiver 106. For example, if the caregiver generates an initial diagnosis through an examination of the patient 102, that diagnosis can be provided by the caregiver as contextual data. Other physical features associated with the patient 102 can also be captured by the caregiver, such as known disease states or other medical conditions (e.g., drugs taken, prior addictions, etc.).

Other contextual data can include information associated with how and where the image data is captured. For example, the type of device and software used to capture the data can be recorded. Further, the environment in which the images are captured can be saved, such as home, clinic, or hospital.

In another embodiment, contextual data associated with how the caregiver 106 captured the images is stored. For example, if the caregiver retook multiple images, that data is stored. Further, if the caregiver only selects certain images for storage, the process by which the caregiver makes those selections is stored. Aspects associated with images that are stored and/or discarded by the caregiver can be saved. Further, the caregiver's manipulation of the images, such as how long the caregiver reviewed each image, can be captured.

For example, during or after image capture, the caregiver 106 can review each image. The caregiver can decide whether to store each image. The caregiver can also provide comments on the images. The manipulation of the images by the caregiver can be stored as contextual data.

The contextual data that is captured by the caregiver 106 at the time of imaging is stored or otherwise associated with the captured images. For example, the contextual data can be stored as metadata that is associated with the images captured by the caregiver. The contextual data can also include the photo metadata already associated with the captured images, such as date/time captured, resolution, file size, etc. The contextual data is delivered along with the images to the server device 112 for analysis, as described below.

As noted previously, the server device 112 can use the image and contextual data for additional screening and diagnosis purposes. In one example, the server device 112 using artificial intelligence to analyze the images and contextual data. The artificial intelligence can leverage data from many different patients (provided in an anonymous manner) to learn how to diagnose certain disease states.

For instance, the server device 112 can use artificial intelligence to analyze the images of the fundus along with contextual data associated therewith. Based upon this information, the server device 112 can diagnose a disease state, such as diabetic retinopathy. This possible diagnosis can also be provided with an indicator of the likelihood that such a diagnosis is accurate. For example, the server device 112 can provide a diagnosis and an accuracy indicator (e.g., from 1-100, with 1 being the most unsure and 100 being the most sure) indicating the potential accuracy of the proposed diagnosis. In some examples, artificial intelligence implemented on the server device 112 can also suggest one or more additional tests to be done to increase the potential accuracy of the proposed diagnosis.

For example, because this is a multi-class classification problem, the score can be obtained from a level of information entropy contained in the model output (most likely a probability distribution over multiple classes). Potential adjustments over a general information entropy formula may be done. Another possibility is to incorporate the accuracy recorded from the training process for each class.

In some embodiments, the artificial intelligence can also provide feedback on the screening and quality of the images provided. This feedback can include instructions for taking further images and/or providing further contextual data so that the indicator for a particular diagnosis can be increased in accuracy. For example, if the quality of the images are poor, the feedback could include instructions to take further images of higher quality.

One example of the use of artificial intelligence to analysis images of a fundus is provided in U.S. Patent Application No. 62/783,689 filed on Dec. 21, 2018, the entirety of which is hereby incorporated by reference.

The diagnosis and indicator can be delivered to the referral service 116 and/or the caregiver 106 in near real-time once the images and contextual data are provided to the server device 112. In this scenario, the imaging device 104 assists the caregiver in screening the patient 102, and the server device 112 can assist the caregiver in diagnosis of the patient 102 for one or more disease states.

Figure 4:
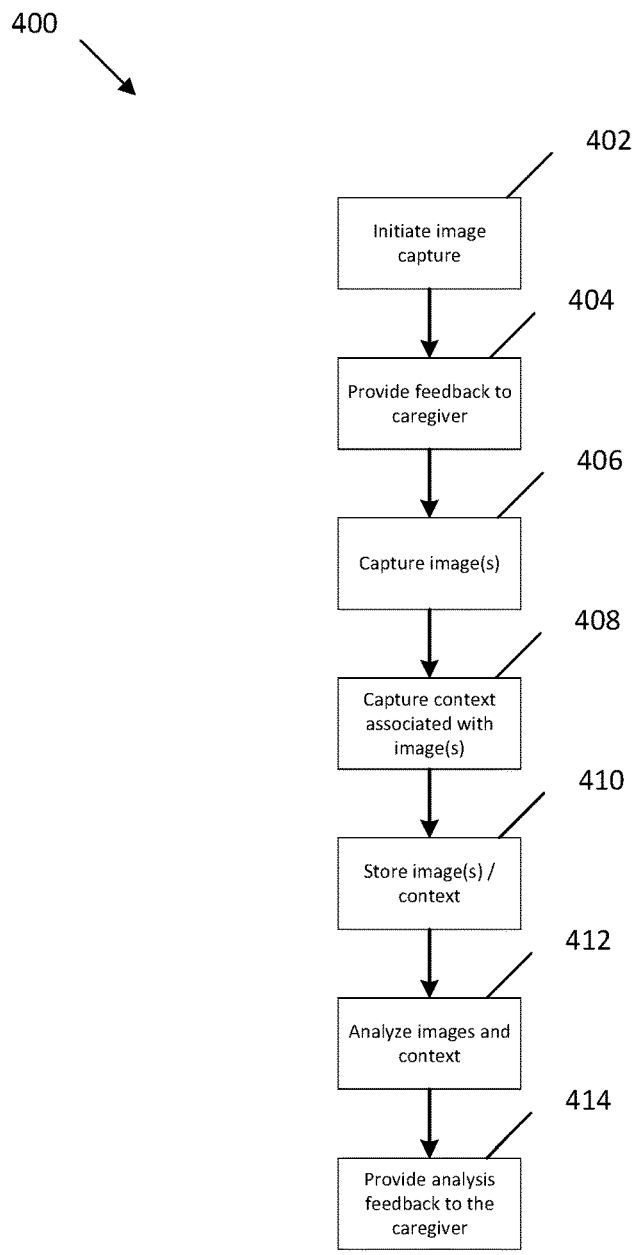
FIG. 4 shows an example method for screening and diagnosing a patient using the system of FIG. 1.

Referring now to FIG. 4, an example method 400 for screening and diagnosing a patient is provided.

At operation 402, the caregiver initiates the capture of one or more images. In the example provided, the images are of the fundus of the eye. Next, at operation 404, the imaging device provides feedback to the caregiver as the images are captured. This feedback can include a workflow for capture of the images, as well as feedback on the quality of the images that are captured. At operation 406, the images are captured by the imaging device.

Next, at operation 408, the contextual data associated with the images is captured. The contextual data can be captured by the imaging device itself and/or from input by the caregiver using the imaging device. Further contextual data can be provided from other sources, such as information about the patient from an EMR.

At operation 410, the images and associated contextual data are stored and forwarded to a remote service (e.g., the cloud) for analysis. At operation 412, artificial intelligence can be used to analyze the images and contextual data associated therewith. The analysis can include a diagnosis and associated accuracy indicator. Finally, at operation 414, the diagnosis and optional accuracy indicator can be provided to the caregiver.

Figure 5:
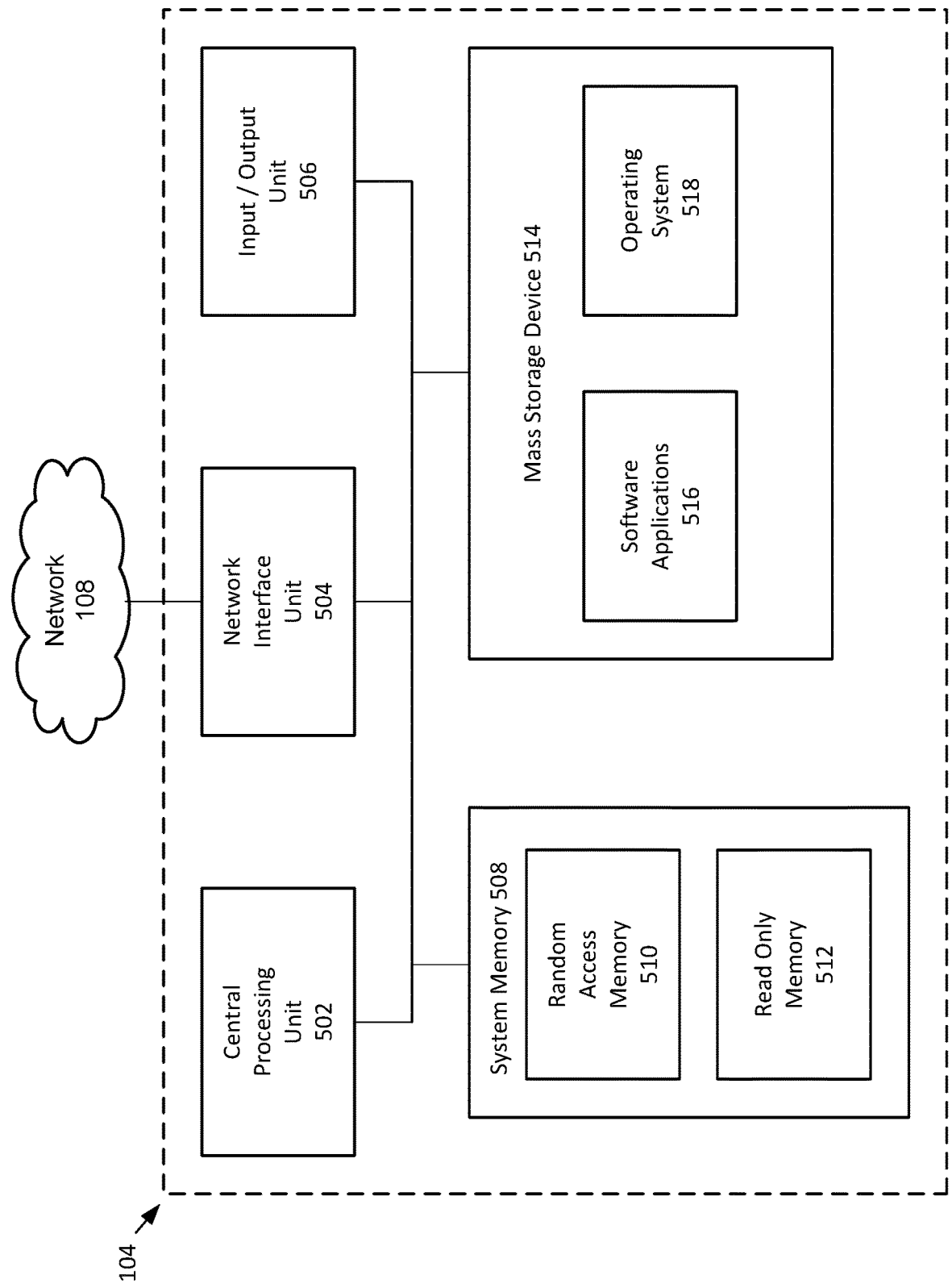
FIG. 5 shows example components of the imaging device of the system of FIG. 1.

Referring now to FIG. 5, example components of the imaging device 104 are provided. The server device 112 can include similar components.

The imaging device 104 may have one or more input devices and one or more output devices configured to communicate with an input/output unit 506. The input devices can be a camera, a keyboard, a mouse, a pen, a sound or voice input device, a touch or swipe input device, etc. Output devices such as a display, speakers, a printer, etc. may also be included. The aforementioned devices are examples and others may be used. The computing device 104 may include a network interface unit 504 allowing communications with other computing devices. Examples include, but are not limited to, RF transmitter, receiver, and/or transceiver circuitry; universal serial bus (USB), parallel, and/or serial ports.

The imaging device includes system memory 508 and a mass storage device 514, both of which can include computer readable media. The term computer readable media as used herein may include non-transitory computer readable media. The system memory 508 may include volatile and nonvolatile, removable and non-removable media implemented in any method or technology for storage of information, such as computer readable instructions, data structures, or program modules. For example, the system memory 508 can include Random Access Memory (RAM) 510 and Read Only Memory (ROM) 512.

The mass storage device 514 may also include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the imaging device 104. Any such computer storage media may be part of the imaging device 104.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

The imaging device 104 also includes a central processing unit (also referred to as a processor) 502 to execute an operating system 518 and/or one or more software applications 516 stored on the mass storage device 514. For example, the central processing unit 514 can execute the software applications 516 to provide one or more workflows that allow the caregiver to accomplish the functionality described herein.

Although the example medical devices described herein are devices used to screen and/or diagnose patients, other types of medical devices can also be used. For example, the different components of the CONNEX™ system from Welch Allyn, Inc. of Skaneateles Falls, NY, such as intermediary servers that communicate with the devices described herein, can also be provided. Embodiments of the present invention may be utilized in various distributed computing environments where tasks are performed by remote processing devices that are linked through a communications network in a distributed computing environment.

The block diagrams depicted herein are just examples. There may be many variations to these diagrams described therein without departing from the spirit of the disclosure. For instance, components may be added, deleted or modified.

While embodiments have been described, it will be understood that those skilled in the art, both now and in the future, may make various improvements and enhancements can be made. The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention.

The claimed inventions should not be construed as being limited to any embodiment, example, or detail provided in this application. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed inventions and the general inventive concepts embodied herein.

What is claimed is:

1. A device configured to capture an image of a patient, the device comprising:
    a camera configured to capture the image of the patient;
    at least one processor; and
    at least one system memory encoding instructions which, when executed by the at least one processor, cause the device to:
        capture contextual data associated with the image, wherein the contextual data includes a process by which a caregiver has selected images for storage and discard, and wherein the contextual data further includes manipulation data relating to manipulations of the image performed by the caregiver;
        provide feedback to the caregiver relating to a quality of the image as the image is captured, wherein the feedback includes at least one recommendation to improve the quality of the image;
        allow the caregiver to select the image to be stored;
        forward the image and the contextual data to a remote server for processing using artificial intelligence;
        receive a proposed diagnosis and an accuracy indicator indicating an accuracy of the proposed diagnosis determined by the artificial intelligence on the remote server, the proposed diagnosis being based upon the image and the contextual data, and the accuracy indicator being a score within a range having a minimum score and a maximum score; and
        receive a recommendation determined by the artificial intelligence on the remote server, the recommendation including a suggestion to perform one or more additional tests to be done by the device to increase the accuracy indicator of the proposed diagnosis, the one or more additional tests including taking additional images of the patient using the camera of the device and providing additional contextual data to increase the accuracy indicator of the proposed diagnosis.

2. The device of claim 1, wherein the minimum score indicates less certainty and the maximum score indicates more certainty regarding the potential accuracy of the proposed diagnosis.

3. The device of claim 1, wherein the proposed diagnosis is a multi-class classification.

4. The device of claim 1, wherein the at least one system memory encodes further instructions which, when executed by the at least one processor, cause the device to receive a second diagnosis from a referral service.

5. A device configured to process a fundus image of a patient, the device comprising:
    at least one processor; and
    at least one system memory encoding instructions which, when executed by the at least one processor, cause the device to:
        receive an image of a fundus of the patient, the image of the fundus captured by a second device;
        receive contextual data associated with the image, wherein the contextual data includes a process by which a caregiver has selected images for storage and discard, and wherein the contextual data further includes manipulation data relating to manipulations of the image performed by the caregiver;
        receive feedback relating to a quality of the image as the image is captured, wherein the feedback includes at least one recommendation to improve the quality of the image;
        use artificial intelligence to develop a proposed diagnosis based upon the image and the contextual data;
        calculate an accuracy indicator indicating an accuracy of the proposed diagnosis, the accuracy indicator being within a range having a minimum score and a maximum score; and
        suggest one or more additional tests using the artificial intelligence, the one or more additional tests to be done by the second device to increase the accuracy indicator of the proposed diagnosis including taking additional images by the second device and providing additional contextual data to increase the accuracy indicator of the proposed diagnosis.

6. The device of claim 5, wherein the minimum score indicates less certainty and the maximum score indicates more certainty regarding the potential accuracy of the proposed diagnosis.

7. The device of claim 5, wherein the proposed diagnosis is a multi-class classification.

8. The device of claim 5, wherein the at least one system memory encodes further instructions which, when executed by the at least one processor, cause the device to forward the image to a referral service for a second diagnosis.

9. A method for diagnosing a disease associated with a fundus of a patient, the method comprising:
    receiving an image of the fundus of the patient, the image of the fundus captured by a device;
    receiving contextual data associated with the image, wherein the contextual data includes a process by which a caregiver has selected images for storage and discard, and wherein the contextual data further includes manipulation data relating to manipulations of the image performed by the caregiver;
    receiving feedback relating to a quality of the image as the image is captured, wherein the feedback includes at least one recommendation to improve the quality of the image;
    using artificial intelligence to develop a proposed diagnosis based upon the image and the contextual data;
    calculating an accuracy indicator indicating an accuracy of the proposed diagnosis, the accuracy indicator being within a range having a minimum score and a maximum score; and suggesting one or more additional tests using the artificial intelligence, the one or more additional tests to be done by the device to increase the accuracy indicator of the proposed diagnosis including taking additional images by the device and providing additional contextual data to increase the accuracy indicator of the proposed diagnosis.

10. The method of claim 9, wherein the minimum score indicates less certainty and the maximum score indicates more certainty regarding the potential accuracy of the proposed diagnosis.

11. The method of claim 9, forwarding the image to a referral service for a second diagnosis.

\* \* \* \* \*